United States Patent [19]

Coffee

[11] 4,262,520

[45] Apr. 21, 1981

[54] SUPPLEMENTAL WEIGHT PERCENT ANALYSIS FOR CHROMATOGRAPHY

[75] Inventor: Robert D. Coffee, Dallas, Tex.

[73] Assignee: Atlantic Richfield Company, Los Angeles, Calif.

[21] Appl. No.: 107,952

[22] Filed: Dec. 28, 1979

[51] Int. Cl.³ ............................................. G01N 5/04
[52] U.S. Cl. ........................................ 73/1 G; 73/23; 73/23.1
[58] Field of Search ........................ 73/1 G, 23, 23.1; 23/230 PC, 232 R, 232 C; 422/68, 80, 83, 89

[56] References Cited

U.S. PATENT DOCUMENTS

| 3,204,448 | 9/1965 | Thorburn et al. | 73/23.1 |
| 4,057,995 | 11/1977 | Kleiss | 73/23 |

Primary Examiner—Stephen A. Kreitman
Attorney, Agent, or Firm—M. David Folzenlogen

[57] ABSTRACT

In chromatography, the weight percent of higher boiling hydrocarbons is estimated by comparing areas under the certain segments of chromatograms. This procedure is subject to both human and equipment errors. A supplemental procedure for measuring the percent of higher boiling point hydrocarbons is disclosed. This procedure is specially related to chromatography and uses gradual heating and inert gas vaporization of the lower boiling point hydrocarbons in the sample material. In the procedure, a sample of the same hydrocarbon tested in the chromatograph is weighed and is heated to the same temperature as used in the chromatograph while flowing inert gas, e.g. helium, past the sample. After reaching this temperature, gas flow is continued for at least eight minutes. The residual sample is weighed and the difference used to determine and check the chromatograph estimation. The procedure may be checked with a calibrated sample of hydrocarbons boiling at and below the final maximum test temperature. The procedure may be performed simultaneously on both the unknown sample and the calibrated sample.

5 Claims, 1 Drawing Figure

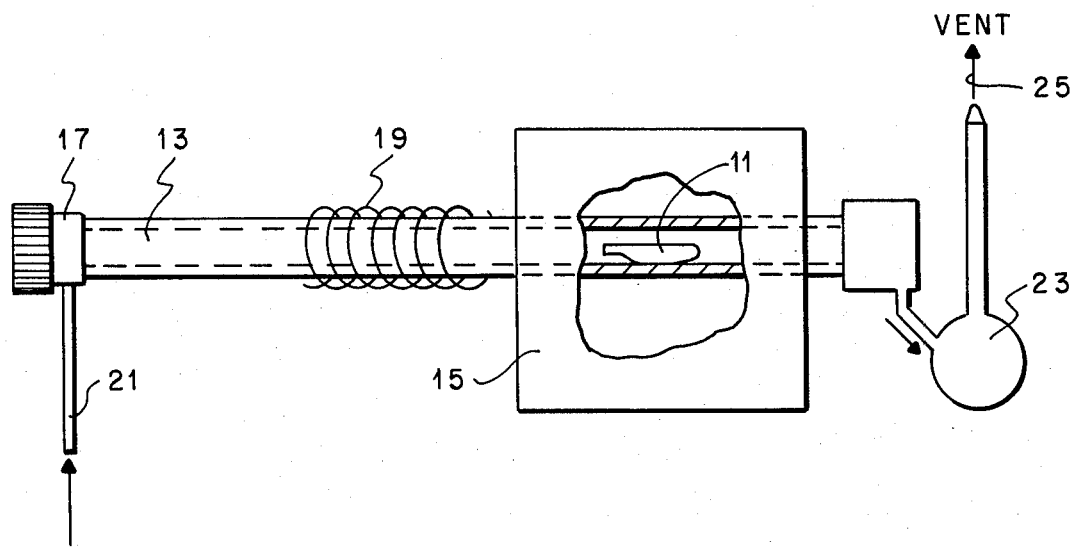

ABSTRACT

SUPPLEMENTAL WEIGHT PERCENT ANALYSIS FOR CHROMATOGRAPHY

BACKGROUND OF THE INVENTION

This invention pertains to a special gravimetric measurement of the percent of high boiling point hydrocarbons in a way that the measurement is related to and useful in chromatographic analysis of the same hydrocarbon. More particularly, the measurement uses inert gas sweep and similar temperatures, thereby allowing direct correlation of results.

The American Society for Testing and Materials has a "Standard Test Method for BOILING RANGE DISTRIBUTION OF PETROLEUM FRACTIONS BY GAS CHROMATOGRAPHY", ANSI/ASTM D 2887-73, published October 1973, pages 789–797. This test method covers determinations of the boiling range distribution of petroleum products whose final boiling point is 1000° F. (538° C.) or less at atmospheric pressure. The same ASTM manual at pages 716-722 sets forth a "Proposed Test Method for BOILING RANGE DISTRIBUTION OF CRUDE PETROLEUM BY GAS CHROMATOGRAPHY", published November 1976. This proposed test has no status as an ASTM standard and covers crude petroleum with high-boiling fractions. In the procedure a sample of the unknown petroleum is injected with a micro syringe and the temperature of the test sample raised at a reproducible rate while the sample is being swept with an inert carrier gas. The type gas depends on the type of detector. For thermal conductivity detectors, helium or hydrogen is used. For flame ionization detectors, nitrogen, helium or argon is used. The area under a chromatogram is recorded with time and compared to the chromatogram of a known calibrated paraffinic hydrocarbon mixture. An internal standard of at least four paraffinic hydrocarbons, preferably above $C_{14}$ is also used. The chromatographic procedure raises the sample to a predetermined equipment temperature which is equated to a much higher maximum test boiling point temperature, e.g. 1000° F. When the hydrocarbon sample has components which do not vaporize or are not segregated by the chromatograph, it is necessary to estimate the percentage of the higher boiling point hydrocarbons by comparing the areas under known and unknown chromatograms. Chromatographic analyses are time consuming. The calculation is subject to significant error both in sample handling and injection and in equipment operation. It would, therefore, be useful to have a simple procedure for checking the higher boiling fraction. Ordinary, gravimetric techniques are not suitable for this purpose because of carbonization, splattering, and other similar problems. Moreover, standard gravimetric techniques are not related to the chromatographic technique where the sample is not actually raised to the boiling point temperature of the hydrocarbon being measured at any given moment.

SUMMARY OF THE INVENTION

The weight fraction of a high boiling point fraction is measured gravimetrically as an aid to a gas chromatography test of a hydrocarbonaceous liquid having a fraction that boils above the maximum test boiling point temperature equivalent to the maximum equipment temperature used in the chromatography test. The weight fraction is determined by weighing a sample of the hydrocarbon before and after the hydrocarbon is heated to the same equipment temperature used in the chromatograph while flowing an inert gas, e.g. helium, past the sample. The inert gas continually sweeps the surface of the sample liquid thereby maintainning an essentially zero partial pressure of the hydrocarbons in the gas above the sample. This eliminates the need for heating the sample to carbonization temperatures and avoids the other problems which would be encountered if standard gravimetric analysis techniques were used. Inert gas flow is continued for at least 8 minutes after the desired temperature is reached. For greater accuracy, a known hydrocarbon sample of lower boiling point material is tested in the same manner to determine if any residue is left from the lower boiling materials.

BRIEF DESCRIPTION OF THE DRAWING

The drawing illustrates suitable equipment for use in this supplemental test procedure.

DETAILED DESCRIPTION

In the analysis of a hydrocarbonaceous liquid like crude petroleum oil by a gas chromatograph, a sample of the liquid is injected into the chromatograph with a micro syringe. The temperature of the injected liquid is raised at a reproducible rate to a maximum equipment test temperature while the sample is being swept with an inert gas, usually helium, through the chromatograph. The maximum test temperature is predetermined by the user who sets the level through a control. Generally, the maximum equipment temperature is 400° C. (752° F.). A maximum test temperature of 350° C. is frequently used for crude oil samples. A standard liquid of a mixture of known paraffinic hydrocarbons is also run. By comparing the two chromatograms, the maximum equipment test temperature may be equated to the weight percent fraction of a hydrocarbon whose boiling point is well above 350° C. or 662° F., for example, 950° F. The weight percent of hydrocarbons in the sample boiling above this point are calculated in several ways which involve the use of calibrated liquids. The chromatographic procedure is subject to human error and it is not always easy to detect errors.

A supplemental analysis procedure is performed to determine the weight fraction of the higher boiling point portion of the sample liquid not measured by the chromatograph. This supplemental analysis aids in correlation and checking of chromatographic results. Accordingly, a test sample of the hydrocarbonaceous liquid is weighed in tared crucible 11. The crucible is then inserted into tube 13 and positioned in oven 15 which is suitable for slowly raising the temperature of the sample in the crucible. As shown, the end of the tube is sealed with closure 17. Ahead of oven 15 is surface heater 19 which serves to preheat an inert gas injected into tube 13 by way of gas inlet line 21. The gas is inert to the hydrocarbons in the sample. Typical inert gases are helium, argon and nitrogen. Helium is preferred because of its similarity to the inert gas used in the corresponding chromatographic analysis.

The liquid sample is gradually heated to the same maximum test temperature used in the chromatograph, for example, 350° C. While the sample is being heated and for at least 8 minutes after this temperature is reached, inert gas is flowed past the surface of the sample into collection bottle 23 where the hydrocarbon vapors are condensed and the inert gas is vented overhead through outlet 25. This prevents pollution.

After the sample area has been heated to the same temperature as that used in the chromatographic test and the flow of inert gas discontinued, the crucible is cooled and weighed. The ratio of the weight of the residual hydrocarbon liquid to the weight of the original sample determines the weight fraction of hydrocarbonaceous materials not measured in the chromatographic analysis.

For control and calibration purposes, a similar procedure may be carried out on an appropriate weight sample of known hydrocarbons covering the boiling range through the maximum test boiling point temperature. For example, a sample of the calibration standard used in the chromatograph may be used. If any residual portion is left, it is then deducted from the weight of the residual portion of the test sample before the weight fraction is determined. For accuracy purposes, it is much preferred that the calibration sample and the test sample be heated and purged with inert gas flow simultaneously.

Reasonable variations and modifications are practical within the scope of this disclosure without departing from the spirit and scope of the appended claims. For example, the invention was illustrated with a modified standard macrocombustion apparatus, but any suitable apparatus may be used. Moreover, any number of test samples and/or calibration samples may be run simultaneously provided that the partial pressure of the hydrocarbons in the inert purge gas is kept very low.

The embodiments of the invention in which an exclusive property or privilege is claimed are defined as follows:

1. In the analysis of a hydrocarbonaceous liquid by gas chromatography wherein the liquid is raised to a predetermined equipment temperature which is equated to a maximum test boiling point temperature, and wherein said hydrocarbonaceous liquid has a high boiling point portion that is not measured during the chromatographic analysis, a method of determining the weight fraction of said high boiling point portion in said hydrocarbonaceous liquid comprising:
   (a) weighing a test sample of said hydrocarbonaceous liquid;
   (b) heating said weighed test sample while flowing an inert gas past said weighed test sample to said predetermined equipment temperature,
   (c) continuing said inert gas flow for at least 8 minutes after said predetermined equipment temperature is reached, thereby creating a residual portion of said weighed test sample; and
   (d) weighing said residual portion and determining the ratio of the weight of said residual portion to the weight of said weighed test sample, thereby determining the weight fraction of said hydrocarbonaceous liquid that is not measured in said chromatographic analysis.

2. The method of claim 1 wherein the inert gas is helium.

3. The method of claim 1 wherein the method includes the following steps:
   (e) weighing a calibration sample of a mixture of hydrocarbons of known boiling point covering the boiling range through said maximum test boiling point temperature;
   (f) heating said calibration sample at the same rate to the same temperature as said weight sample was heated in step (b) while flowing said inert gas past said weighed calibration sample at the same rate and for the same time as said inert gas was flowed in step (b), and
   (g) weighing any residual portion of said calibration sample and subtracting the weight of any said residual portion of said calibration sample from said residual portion of said test sample prior to determining said weight fraction in step (d).

4. The method of claim 3 wherein the inert gas is helium.

5. The method of claim 3 wherein steps (b) and (f) are performed at the same time.

* * * * *